United States Patent [19]

Ort et al.

[11] Patent Number: 5,447,903

[45] Date of Patent: Sep. 5, 1995

[54] HERBICIDAL ACTIVE SUBSTANCE COMBINATIONS

[75] Inventors: Oswald Ort, Kelkheim; Lothar Willms, Hillscheid; Hans-Joachim Zeiss, Sulzbach; Klaus Bauer, Hanau; Hermann Bieringer, Eppstein/Taunus, all of Germany

[73] Assignee: Hoechst Aktiengesellschaft, Frankfurt am Main, Germany

[21] Appl. No.: 842,356

[22] PCT Filed: Oct. 12, 1990

[86] PCT No.: PCT/EP90/01720

§ 371 Date: Mar. 25, 1992

§ 102(e) Date: Mar. 25, 1992

[87] PCT Pub. No.: WO91/05469

PCT Pub. Date: May 2, 1991

[30] Foreign Application Priority Data

Oct. 18, 1989 [DE] Germany ............... 39 34 706.0
Nov. 25, 1989 [DE] Germany ............... 39 39 094.2

[51] Int. Cl.⁶ ............... A01N 43/38; A01N 43/76; A01N 31/08; A01N 35/06
[52] U.S. Cl. ............... 504/138; 504/270; 504/348; 504/350
[58] Field of Search ............... 71/103, 90, 123, 88; 504/138, 140, 145, 270, 348, 350

[56] References Cited

U.S. PATENT DOCUMENTS

| | | | |
|---|---|---|---|
| 4,130,413 | 12/1978 | Handte et al. | 71/90 |
| 4,531,969 | 7/1985 | Nestler et al. | 71/108 |
| 4,780,127 | 10/1988 | Michaely et al. | 71/103 |
| 4,954,529 | 9/1990 | Koch et al. | 514/594 |

FOREIGN PATENT DOCUMENTS

| | | |
|---|---|---|
| 0060429 | 9/1982 | European Pat. Off. . |
| 0090262 | 10/1983 | European Pat. Off. . |
| 0135191 | 3/1985 | European Pat. Off. . |
| 0137963 | 4/1985 | European Pat. Off. . |
| 0083648 | 6/1986 | European Pat. Off. . |
| 0186118 | 7/1986 | European Pat. Off. . |
| 0186119 | 7/1986 | European Pat. Off. . |
| 0186120 | 7/1986 | European Pat. Off. . |
| 0230596 | 5/1987 | European Pat. Off. . |
| 0274634 | 7/1988 | European Pat. Off. . |
| 0298680 | 1/1989 | European Pat. Off. . |
| 332133A1 | 9/1989 | European Pat. Off. . |
| 0319075 | 5/1990 | European Pat. Off. . |
| 3108873A1 | 9/1982 | Germany . |
| 53-98936 | 8/1978 | Japan . |
| 57-193406 | 11/1982 | Japan . |
| 58-110591 | 7/1983 | Japan . |
| 60-78965 | 5/1985 | Japan . |
| 60-87239 | 5/1985 | Japan . |
| 60-116602 | 6/1985 | Japan . |
| 60-139603 | 7/1985 | Japan . |
| 61-152642 | 7/1986 | Japan . |
| 61-152649 | 7/1986 | Japan . |
| 62-145003 | 6/1987 | Japan . |
| 62-286903 | 12/1987 | Japan . |
| 63-211250 | 9/1988 | Japan . |
| WO83/00329 | 2/1983 | WIPO . |

OTHER PUBLICATIONS

Gray's Manual of Botany, p. lxi, lxii (1970).
Chemical Abstracts, vol. 111, No. 25, Dec. 18, 1989, pp. 260–261, American Chemical Society.
Chemical Abstracts, vol. 107, No. 13, Sep. 28, 1987; pp. 221–222, American Chemical Society.

*Primary Examiner*—Richard L. Raymond
*Assistant Examiner*—Deborah Lambkin
*Attorney, Agent, or Firm*—Curtis, Morris & Safford

[57] ABSTRACT

Combinations of active substances of the formula (I)

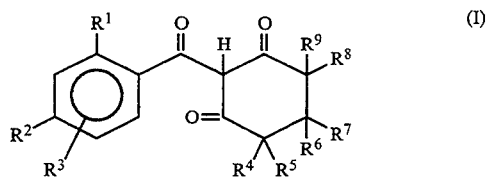

where
R¹ is halogen, lower alkoxy, alkyl or haloalkyl, NO₂, CN, (S(O)ₙR¹⁰ [sic],
R² and R³ are H, halogen, lower alkyl, alkoxy, ha-
(Abstract continued on next page.)

loalkoxy or haloalkyl, CN, $NO_2$, $S(O)_m R^{11}$, $NR^{11}R^{13}$, $NR^{14}-COR^{15}$, $CO-R^{16}$, $R^4$ and $R^6-R^9$ are H or lower alkyl, $R^5$ is H, lower alkyl or alkyl—O—CO—, $R^{10}$ is lower alkyl, haloalkyl or alkoxy, $R^{11}$ is lower alkyl or haloalkyl or phenyl, benzyl or $NR^{17}R^{18}$, $R^{12}$ and $R^{13}$ are H or lower alkyl, $R^{14}$ is H or lower alkyl, $R^{15}$ is lower alkyl, $R^{16}$ is H, lower alkyl, haloalkyl or alkoxy, $R^{17}$ and $R^{18}$ are H or lower alkyl, n and m in each case are 0 to 2, with herbicides from the group comprising fenoxaprop-ethyl, fenoxaprop-P-ethyl, quinchlorac, molinate, thiobencarb, butachlor, pretilachlor, mefenacet, esprocarb, dimepiperate, HW-52; cinmethylin, anilophos, benfuresate, triazofenamide, benzofenap, pyrazoxyfen and TFH-450, have advantages on application, for example a synergistic increase in action, in particular in the case of important weeds in cereals, maize and rice.

13 Claims, No Drawings

HERBICIDAL ACTIVE SUBSTANCE COMBINATIONS

The invention is in the area of the plant protection agents which can be used against monocotyledon and dicotyledon weeds.

EP-A 0,137,963, EP-A 0,186,118, EP-A 0,274,634, EP-A 0,298,680 and U.S. Pat. No. 4,780,127 disclose 2-benzoylcyclohexanedione derivatives with which a broad range of monocotyledon and dicotyledon weeds can be controlled. They can be employed as soil-acting herbicide and also via the shoot or leaf and show, in particular, also a high selectivity in monocotyledon crop plants such as cereals, maize and rice.

There exist, however, various economically highly important monocotyledon weeds in cereals and also in maize and rice, such as, for example, *Alopecurus myosuroides, Avena fatua, Echinochloa crus galli* or *Setaria viridis*, which cannot be controlled in an ideal manner if only the abovementioned compounds are used.

Surprisingly, some herbicidal active substances have now been found in biological trials which, when used together with the abovementioned compounds, have pronounced synergistic actions as regards the effectiveness against weeds.

The present invention therefore relates to herbicidal agents which contain an effective amount of one or more compounds of the formula (I) or of salts thereof (type A compounds)

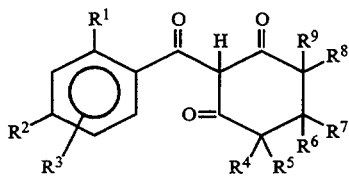

where
- $R^1$ is halogen, ($C_1$–$C_4$)alkoxy, ($C_1$–$C_4$)alkyl, ($C_1$–$C_4$)haloalkyl, —$NO_2$, —CN or $S(O)_n R^{10}$;
- $R^2$ and $R^3$ independently of one another are hydrogen, halogen, ($C_1$–$C_4$)alkyl, ($C_1$–$C_4$)alkoxy, ($C_1$–$C_4$)haloalkoxy, ($C_1$–$C_4$)haloalkyl, —CN, —$NO_2$, —$S(O)_m$—$R^{11}$, —$NR^{12}R^{13}$, —$NR^{14}$—CO—$R^{15}$;
- $R^4$, $R^6$, $R^7$, $R^8$ and $R^9$ independently of one another are hydrogen, ($C_1$–$C_4$) alkyl or —CO—$R^{16}$;
- $R^5$ is hydrogen, ($C_1$–$C_4$)alkyl or —CO—O—($C_1$–$C_4$)alkyl;
- $R^{10}$ is ($C_1$–$C_4$)alkyl, ($C_1$–$C_4$)haloalkyl or ($C_1$–$C_4$)alkoxy;
- $R^{11}$ is ($C_1$–$C_4$) alkyl, ($C_1$–$C_4$) haloalkyl, phenyl, benzyl or —$NR^{17}R^{18}$;
- $R^{12}$ and $R^{13}$ independently of one another are hydrogen or ($C_1$–$C_4$)alkyl;
- $R^{14}$ is hydrogen or ($C_1$–$C_4$)alkyl;
- $R^{15}$ is ($C_1$–$C_4$)alkyl;
- $R^{16}$ is hydrogen, ($C_1$–$C_4$)alkyl, ($C_1$–$C_4$)haloalkyl or ($C_1$–$C_4$)alkoxy;
- $R^{17}$ and $R^{18}$ independently of one another are hydrogen or ($C_1$–$C_4$)alkyl and
- n and m independently of one another are 0, 1 or 2, in combination with one or more of the following compounds II-XX (type B compounds):

Ethyl D-2-[4-(6-chlorobenzoxazol-2-yloxy)phenoxy]propionate (II),

Ethyl D,L-2-[4-(6-chlorobenzoxazol-2-yloxy)phenoxy]propionate (III),

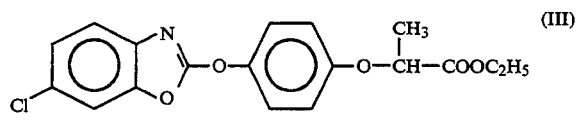

3,7-Dichloroquinoline-8-carboxylic acid (IV) and salts thereof,

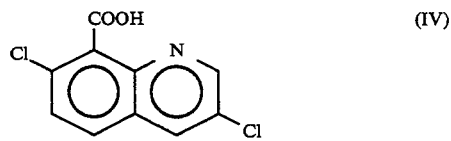

N-(ethylthiocarbonyl)azepane (V),

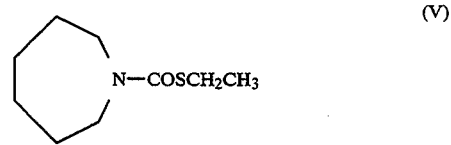

S-4-chlorobenzyl N,N-diethylthiocarbamate (VI),

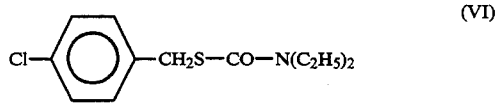

N-(butoxymethyl)-2-chloro-N-(2,6-diethylphenyl)acetamide (VII),

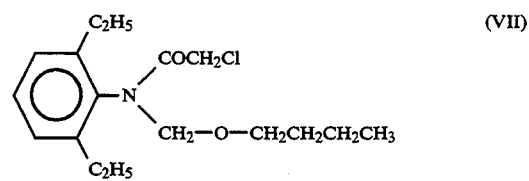

N-(2-propoxyethyl)-2-chloro-N-(2,6-diethylphenyl)acetamide (VIII),

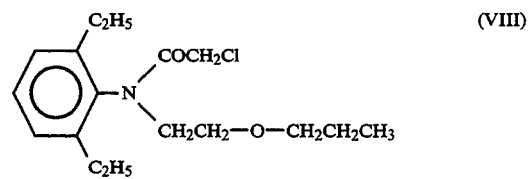

3,5-Bis(methylthiocarbonyl)-2-difluoromethyl-4-(2-methylpropyl)-6-trifluoromethylpyridine (IX),

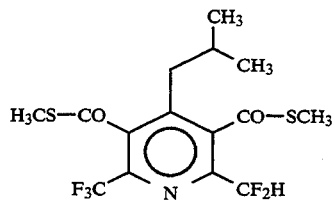

2-(1,3-benzothiazol-2-yloxy)-N-methylacetanilide (X),

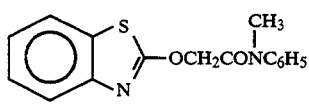

S-benzyl N-ethyl-(1,2-dimethylpropyl)thiocarbamate (XI),

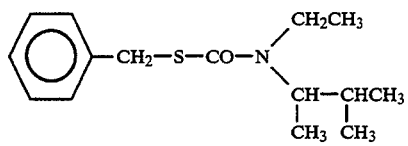

N-(2-phenylprop-2-ylthiocarbonyl)piperidine (XII),

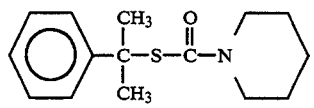

HW-52, i.e. 4-ethoxymethoxy-N-(2,3-dichlorophenyl)benzamide (XIII),

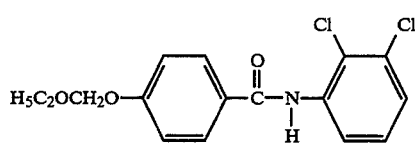

cinmethylin, chemical name exo-1-methyl-4-(1-methylethyl)-2-(2-methylphenylmethoxy)-7-oxabicyclo-[2.2.1]-heptane (XIV),

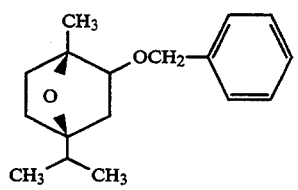

anilofos, S-[2-[(4-chlorophenyl)(1-methylethyl)amino]-2-oxoethyl]O,O-dimethyl phosphorodithioate (XV)

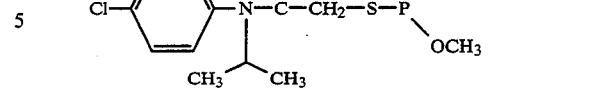

benfuresate, 2,3-dihydro-3,3-dimethyl-5-benzofuranylethanesulfonate (XVI)

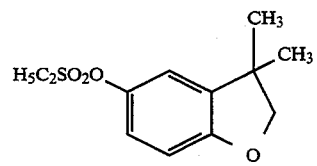

KNW-242, triazofenamide, 1-(3-methylphenyl)-5-phenyl-1H-1,2,4-triazol-3-carboxamide (XVII)

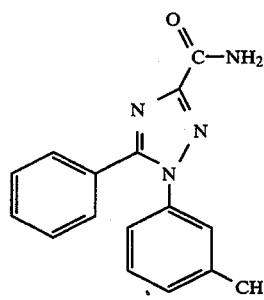

benzofenap, 2-[4-(2,4-dichloro-m-toluoyl)-1,3-dimethylpyrazol-5-yloxy]-4-methylacetophenone (XVIII)

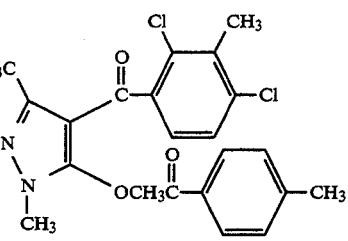

pyrazoxyfen, 2-[4-(2,4-dichlorobenzoyl)-1,3-dimethylpyrazol-5-yloxy]-acetophenone (XIX)

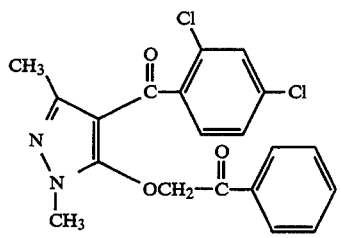

TFH-450, 3-(2,6-diethylphenylsulfonyl)-1-(N-ethyl-N-methylaminocarbonyl)-1,2,4-triazole (XX)

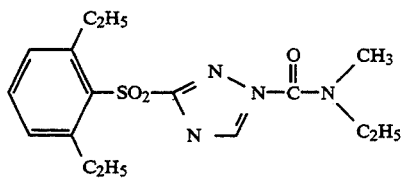

The compounds of the formula (I) are disclosed in the publications mentioned at the outset. Compound (IV) is known from British Crop Protection Conference-Weeds, 1985, p. 77–83, as BAS 514 H (quinchlorac). Compounds (II) and (III), (V)–(VIII), (XV) and (XVI) are all described in "The Pesticide Manual", British Crop Protection Council, 8th Ed., 1987; see (III) ("fenoxaprop-ethyl") p. 379; (V) ("molinate") p. 578; (VI) ("thiobencarb") p. 796; (VII) ("butachlor") p. 106; (VIII) ("pretilachlor") p.689; (X) ("mefenacet") p. 526; (XV) ("anilofos") p. 30; (XVI) ("benfuresate") p. 857. Compound (IX) is known as "MON 7200" and described in "Proceedings of the 11th Asian-Pacific Weed Science Society Conference 1987, page 455–460". Compounds (XI) and (XII) are described in "Short Review of Herbicides 1986" 5th edition 1985, Hodogaya Chemical Co. Ltd., Japan, pages 110 or 108, under the names SC-2957 (esprocarb) or MY-93, kayamate. MY-93 is also termed dimepiperate or yukamate (see in "Agricultural Chemicals" Thomson Publications 1989–90, U.S.A. p. 252).

Compound (XIII) (HW-52) is known from Shokubutsu no Kagakin Chosetsu 18 (2), 151–60 (1983); CA 101 (3): 18948d.

Compound (XIV) ("cinmethylin") is known from R. G. Jones in "Pest Management in Rice"; B. T. Grayson, M. B. Green, L. G. Copping (Editors); Society of Chemical Industry; Elsevier Science Publish; England 1990; ISBN 1-85166-514-5.

Compound (XVII) ("triazofenamide") is known from Document Iso/TC 81 N 875, British Standards Institution, June 1987.

Compounds (XVIII) ("benzofap") and (XIX) ("pyrazoxyfen") are known from "The Agrochemicals Handbook", 2nd Edition, The Royal Society of Chemistry, Cambridge, England.

Compound (XX) is disclosed in EP-A 332,133.

Herbicidal agents according to the invention with compounds of the abovementioned formula (I) or salts thereof where $R^1$ is fluorine, chlorine, bromine, iodine, methoxy, nitro, cyano or —S(O)$_n$R$^{10}$, $R^2$ and $R^3$ independently of one another are hydrogen, fluorine, chlorine, bromine, iodine, methyl, methoxy, trifluoromethoxy, cyano, nitro, trifluoromethyl, —SO$_2$R$^{11}$, —NR$^{12}$R$^{13}$, —N(CH$_3$)—CO—R$^{14}$ or —CO—O—(C$_1$-C$_4$)alkyl and $R^4$, $R^5$, $R^6$, $R^7$, $R^8$ and $R^9$ independently of one another are hydrogen or methyl and $R^{10}$, $R^{11}$, $R^{12}$, $R^{13}$, $R^{14}$ and n are as defined above, are of particular interest.

Herbicidal agents according to the invention with compounds of the formula (I) in which $R^2$ and $R^3$ independently of one another are hydrogen, fluorine, chlorine, bromine, —N(CH$_3$)$_2$, methoxy, nitro, —SO$_2$CH$_3$, —SO$_2$CH$_2$Cl, —SO$_2$N(CH$_3$)$_2$ or trifluoromethyl and n is 2, and $R^1$, $R^4$, $R^5$, $R^6$, $R^7$, $R^8$ and $R^9$ are as defined above, are particularly preferred.

The compounds of the formula (I) can be present in various tautomeric structures (keto/enol tautomery) and have a very acidic hydrogen atom on the methine group between the three carbonyl groups, which hydrogen atom can be replaced by a cation suitable for agriculture. The salts which are then present are generally metal salts, in particular alkali metal salts, alkaline earth metal salts, optionally substituted or unsubstituted ammonium, sulfonium or phosphonium salts in which the substituents can be aliphatic or aromatic radicals. Suitable bases for preparing the salts according to the invention are, for example, alkali metal carbonates such as potassium carbonate, alkali metal hydroxides and alkaline earth metal hydroxides, ammonia or ethanolamine.

Alkyl radicals are understood as meaning radicals having the stated number of carbon atoms. The radicals can be straight-chain or branched. The most common radicals are, for example, methyl, ethyl, n-propyl, isopropyl, n-butyl, isobutyl, sec.-butyl or tert-butyl. Halogen is understood as meaning fluorine, chlorine, bromine or iodine. Haloalkyl radicals can be monosubstituted or polysubstituted by halogen, i.e. they can also be perhalogenated.

Examples of particularly suitable compounds of the formula (I) in the herbicidal mixtures according to the invention are 2-(2-chloro-4-methylsulfonylbenzoyl)-1,3-cyclohexanedione (Ia), 2-(2-nitrobenzoyl)-4,4-dimethyl-1,3-cyclohexanedione (Ib) and 2-(2-(nitrobenzoyl)-5,5-dimethyl-1,3-cyclohexanedione (Ic). The 2-benzoylcyclohexanedione derivatives of the formula (I) have been disclosed, see, for example, the abovementioned EP-A Publications No. 0,137,963, 0,186,118, 0,274,634 and 0,298,680 and U.S. Pat. No. 4,780,127, or they can be prepared by the methods stated in these publications.

The herbicidal agents according to the invention have an excellent herbicidal activity against a broad range of economically important monocotyledon and dicotyledon harmful plants. The active substance combinations also act efficiently on perennial weeds which produce shoots from rhizomes, small rootstocks or other perennial organs and which are difficult to control. In this context, it does not matter whether the substances are applied before sowing, pre-emergence or post-emergence. Specifically, examples may be mentioned of some representatives of the monocotyledon and dicotyledon weed flora which can be controlled by the agents according to the invention, without the enumeration being a restriction to certain species.

Examples of weed species on which the active substance combinations act efficiently are, from amongst the monocotyledons, Echinochloa species and also Cyperus species from the annual sector and from amongst the perennial species perennial Cyperus species and Scirpus species.

In the case of the dicotyledon weed species, the range of action extends to Galium, Viola, Veronica, Lamium, Stellaria, Amaranthus, Sinapis, Ipomoea, Matricaria, Abutilon, Sida etc. from amongst the annuals, and Convolvulus, Cirsium, Rumex, Artemisia etc. in the case of the perennial weeds.

The active substance combinations according to the invention likewise effect outstanding control of weeds which occur under the specific conditions of rice growing, such as, for example, Sagittaria, Alisma, Eleocharis, Scirpus and Cyperus.

Economically important monocotyledon weeds which occur under the specific conditions of maize and rice growing such as, for example, *Alopecurus myosuroides, Avena fatua, Echinochloa crus galli* and *Setaria viridis*, are also controlled.

If the herbicidal agents according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substance combinations are applied post-emergence on the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner by applying the novel agents according to the invention.

Even though the agents according to the invention have an excellent herbicidal activity against monocotyledon and dicotyledon weeds, crop plants of economically important crops, such as, for example, wheat, barley, rye, rice and maize, are damaged not at all, or only to a negligible extent. For these reasons, the agents are highly suitable for selectively controlling undesired plant growth in plantings for agricultural use.

For example, a herbicidal action is achieved when using the active substance combinations according to the invention which exceeds what would have been expected as the additive action of individual components. Such increased actions permit the dosage rates of individual active substances to be reduced considerably. Advantages as regards the action were also found of such a nature that either the long-term action of the combinations is improved or that an enhanced speed of action can be observed. Such properties are therefore novel inventions which mean economical progress and which offer considerable advantages to the user in the practice of weed control, because he is capable of controlling weeds more economically or more rapidly or more permanently and can therefore harvest a higher yield in a stand of crop plants.

It has furthermore been found that there is a pronounced safener or antidote action in a series of the active substance combinations, i.e. the phytotoxic side effects which occur when the active substances are used in crop plants such as, for example, rice, are reduced or entirely avoided.

The mixing ratios of the compounds type A to type B can vary within wide limits, generally between 1:0.5 to 1:200. The mixing ratio is selected as a function of, for example, the other component in the mixture, the development stage of the weeds, the weed spectrum and the climatic conditions.

It is preferred to use mixing ratios type A:type B compounds of 1:1 to 1:100. The dosage rates of the herbicide of type A in the active substance mixtures is preferably between 10 and 500 g/ha, the dosage rates of the compound of type B between 0.02 and 4.0 kg/ha.

The active substance combinations according to the invention can either be a mixed formulation of the two components which are then diluted with water and applied in a customary manner, or they can be prepared as so-called tank mixes by joint dilution, with water, of the separately formulated components.

The compounds of type A and type B or their combinations can be formulated in various manners, depending on the prevailing biological and/or chemico-physical parameters. The following are suitable as possible formulations: wettable powders (WP), water-soluble powders (SP), emulsifiable concentrates (EC), aqueous solutions or concentrates, emulsions (EW), sprayable solutions, capsule suspensions (CS), dispersions on an oil or water base, suspoemulsions, suspension concentrates (SC), dusting powders (DP), solutions which can be mixed with oils (OL), seed-dressing agents, granules (GR) in the form of microgranules, spray granules, coated granules and adsorption granules, granules for broadcasting and soil application, water-soluble granules (SG), water-dispersible granules (WG), ULV formulations, microcapsules and waxes.

These individual types of formulations are known in principle and are described, for example, in: Winnacker-Küchler, "Chemische Technologie [Chemical Technology]", Volume 7, C. Hauser Verlag Munich, 4th Ed. 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives are likewise known and are described, for example, in: Watkins, "Handbook of Insecticide Dust Diluents and Carriers", 2nd Ed., Darland Books, Caldwell N.J.; H. V. Olphen, "Introduction to Clay Colloid Chemistry"; 2nd Ed., J. Wiley & Sons, N.Y., Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte [Surface-active Ethylene Oxide Adducts]", Wiss. Verlagsgesell., Stuttgart 1976; and Winnacker-Küchler, "Chemische Technologie [Chemical Technology]", Volume 7, C. Hauser Verlag Munich, 4th Ed. 1986.

Combinations with other pesticidally active substances such as other herbicides, fungicides or insecticides, as well as fertilizers and/or growth regulators, can also be prepared on the basis of these formulations, for example in the form of a readymix or as a tank mix.

Wettable powders are preparations which are uniformly dispersible in water and which, besides the active substance, also contain wetting agents, for example polyoxethylated alkylphenols, polyoxethylated fatty alcohols or fatty amines, alkane- or alkylbenzenesulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active substance in an organic solvent, for example butanol, cyclohexanone, dimethylformamide, xylene and also higher-boiling aromatic compounds or hydrocarbons, with the addition of one or more emulsifiers. Examples of emulsifiers which can be used are: calcium salts of an alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents can be obtained by grinding the active substance with finely divided solid substances, for example talc or natural clays, such as kaolin, bentonite, pyrophillite or diatomaceous earth.

Granules can be produced either by spraying the active substance onto adsorptive, granulated inert material or by applying active substance concentrates onto the surface of carriers, such as sand, kaolinites or of granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, the agrochemical preparations contain 0.1 to 99 percent by weight, in particular 2 to 95% by weight, of active substance of type A and type B. The concentrations of the active substances of types A and B can vary in the formulations.

The concentration of active substance in wettable powders is, for example, about 10 to 95% by weight, the remainder to 100% by weight is composed of conventional formulation components. In the case of emulsifiable concentrates, the concentration of active substance can be about 1 to 85% by weight, preferably 5 to 80% by weight. Formulations in the form of dusts usually contain about 1 to 25% by weight, mostly 5 to 20% by weight of active substance, sprayable solutions about 0.2 to 25% by weight, preferably 2 to 20% by weight, of active substance. In the case of granules, such as water-dispersible granules, the active substance content depends partly on whether the active compound is liquid or solid and on which granulation auxiliaries and fillers are used. The content in water-dispersible granules is generally between 10 and 90% by weight.

In addition, the active substance formulations mentioned contain, if appropriate, the adhesives, wetting agents, dispersing agents, emulsifiers, penetrants, solvents, fillers or carriers which are conventional in each case.

For use, the formulations, present in commercially available form, are diluted, if appropriate, in a customary manner, for example using water in the case of wettable powders, emulsifiable concentrates, dispersions and water-dispersible granules. Preparations in the form of dusts, granules for soil application and/or broadcasting, and also sprayable solutions are usually not further diluted with other inert substances before use.

The application rate required for the compounds of types A and B varies with the external conditions, such as, inter alia, temperature, humidity, and the nature of the herbicide used.

The examples which follow serve to illustrate the invention:

A. FORMULATION EXAMPLES a) A dusting agent is obtained by mixing 10 parts by weight of an active substance combination according to the invention and 90 parts by weight of talc as inert substance and comminuting the mixture in a hammer mill.

b) A wettable powder which is readily dispersible in water is obtained by mixing 25 parts by weight of active substances A +B, 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned-disk mill.

c) A dispersion concentrate which is readily dispersible in water is obtained by mixing 20 parts by weight of active substances A +B with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of active substances A+B, 75 parts by weight of cyclohexanone as the solvent and 10 parts by weight of oxethylated nonylphenol as the emulsifier.

e) Water-dispersible granules are obtained by mixing 75 parts by weight of active substances A + B,
10 parts by weight of calcium ligninsulfonate,
5 parts by weight of sodium lauryl sulfate,
3 parts by weight of polyvinyl alcohol and
7 parts by weight of kaolin, grinding the mixture on a pinned-disk mill, and granulating the powder in a fluidized bed by spraying on water as the granulation liquid.

f) Water-dispersible granules are also obtained by homogenizing on a colloid mill and comminuting 25 parts by weight of active substances A + B,
5 parts by weight of sodium 2,2'-dinaphthylmethane-6,6'-disulfonate,
2 parts by weight of sodium oleoylmethyltaurinate,
1 parts by weight of polyvinyl alcohol,
17 parts by weight of calcium carbonate and
50 parts by weight of water, subsequently grinding the mixture on a bead mill, and atomizing and drying the resulting suspension in a spray tower by means of a single-fluid nozzle.

The formulations described under a) to f) are, for example, used for formulating the active substance combinations of Table 1 below (the ratio stated is based on weight):

TABLE 1

| Active substance type A | Active substance type B | Ratio |
| --- | --- | --- |
| Ia | II | 1:1 |
|  |  | 1:2 |
|  |  | 1:10 |
|  |  | 1:100 |
| Ia | III | 1:2 |
|  |  | 1:10 |
|  |  | 1:100 |
| Ia | IV | 1:2 |
|  |  | 1:10 |
|  |  | 1:100 |
| Ia | V | 1:2 |
|  |  | 1:10 |
|  |  | 1:100 |
| Ia | VI | 1:2 |
|  |  | 1;10 |
|  |  | 1:100 |
| Ia | VII | 1:2 |
|  |  | 1:10 |

TABLE 1-continued

| Active substance type A | Active substance type B | Ratio |
|---|---|---|
| Ia | VIII | 1:150 |
|  |  | 1:2 |
|  |  | 1:10 |
| Ia | IX | 1:150 |
|  |  | 1:2 |
|  |  | 1:10 |
| Ia | X | 1:150 |
|  |  | 1:2 |
|  |  | 1:10 |
| Ia | XI | 1:100 |
|  |  | 1:2 |
|  |  | 1:10 |
| Ia | XII | 1:100 |
|  |  | 1:2 |
|  |  | 1:10 |
| Ib | II | 1:100 |
|  |  | 1:1 |
|  |  | 1:2 |
|  |  | 1:10 |
| Ib | III | 1:100 |
|  |  | 1:2 |
|  |  | 1:10 |
| Ib | IV | 1:100 |
|  |  | 1:2 |
|  |  | 1:10 |
| Ib | V | 1:100 |
|  |  | 1:2 |
|  |  | 1:10 |
| Ib | VI | 1:100 |
|  |  | 1:2 |
|  |  | 1:10 |
| Ib | VII | 1:100 |
|  |  | 1:2 |
|  |  | 1:10 |
| Ib | VIII | 1:100 |
|  |  | 1:2 |
|  |  | 1:10 |
| Ib | IX | 1:100 |
|  |  | 1:2 |
|  |  | 1:10 |
| Ib | X | 1:150 |
|  |  | 1:2 |
|  |  | 1:10 |
| Ib | XI | 1:150 |
|  |  | 1:2 |
|  |  | 1:10 |
| Ib | XII | 1:100 |
|  |  | 1:2 |
|  |  | 1:10 |
| Ic | II | 1:100 |
|  |  | 1:1 |
|  |  | 1:2 |
|  |  | 1:10 |
| Ic | III | 1:100 |
|  |  | 1:2 |
|  |  | 1:10 |
| Ic | IV | 1:150 |
|  |  | 1:2 |
|  |  | 1:10 |
| Ic | V | 1:100 |
|  |  | 1:2 |
|  |  | 1:10 |
| Ic | VI | 1:100 |
|  |  | 1:2 |
|  |  | 1:10 |
| Ic | VII | 1:100 |
|  |  | 1:2 |
|  |  | 1:10 |
| Ic | VIII | 1:100 |
|  |  | 1:2 |
|  |  | 1:10 |
| Ic | IX | 1:100 |
|  |  | 1:2 |
|  |  | 1:10 |
| Ic | X | 1:100 |
|  |  | 1:2 |
|  |  | 1:10 |
| Ic | XI | 1:100 |
|  |  | 1:2 |
|  |  | 1:10 |
| Ic | XII | 1:100 |
|  |  | 1:2 |
|  |  | 1:10 |

Analogous formulations are obtained with compounds of the formula I and the compounds of formulae XIII–XX.

B. Chemical Examples

EXAMPLE 1

2-[(2-chloro-4-methylsulfonyl)benzoyl]-1,3-cyclohexanedione 42.5 g of 2-chloro-4-methylsulfonylbenzoic acid were boiled in 160 ml of dioxane with 5 drops of dimethylformamide and 25.1 ml of thionyl chloride until the evolution of gas subsided. The solvent was evaporated with the exclusion of moisture (stripping off on a rotary evaporator). To the oily residue there were added at 0° C. 19.7 g of 1,3-cyclohexanedione in 250 ml of acetonitrile, and 63.1 ml of triethylamine were then added dropwise at this temperature. Stirring was continued for 15 minutes, 15.3 ml of acetone cyanohydrin were added, and the mixture was allowed to stand overnight. The reaction mixture was concentrated under reduced pressure on a rotary evaporator, the residue was taken up in ethyl acetate/water, and the organic phase was washed with 2N hydrochloric acid. The product was extracted from the organic phase using 5% $K_2CO_3$ solution, and precipitated at a pH of 2-3 using concentrated hydrochloric acid, with cooling. After filtration with suction and drying, 48.4 g of 2-[(2-chloro-4-methylsulfonyl)benzoyl]-1,3-cyclohexanedione of melting point 141°–142° C. were obtained (Example No. 1; Table 2).

The compounds listed in Table 2 were obtained analogously:

TABLE 2 continuation [sic]

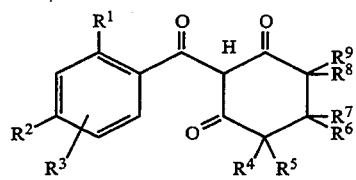

| Example No. | $R^1$ | $R^2$ | $R^3$ | $R^4$ | $R^5$ | $R^6$ | $R^7$ | $R^8$ | $R^9$ | M.p. [°C.] |
|---|---|---|---|---|---|---|---|---|---|---|
| 2 | —$NO_2$ | —Cl | H | H | H | H | H | H | H | 183 |

TABLE 2-continued continuation [sic]

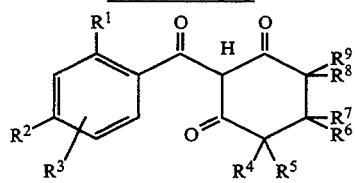

| Example No. | $R^1$ | $R^2$ | $R^3$ | $R^4$ | $R^5$ | $R^6$ | $R^7$ | $R^8$ | $R^9$ | M.p. [°C.] |
|---|---|---|---|---|---|---|---|---|---|---|
| 3 | —NO$_2$ | —H | 2-CH$_3$ | H | H | CH$_3$ | CH$_3$ | H | H | 112 |
| 4 | —Cl | —SO$_2$C$_2$H$_5$ | H | H | H | H | H | H | H | oil |
| 5 | —Cl | —SO$_2$C$_2$H$_5$ | H | H | H | CH$_3$ | CH$_3$ | H | H | oil |
| 6 | —Cl | —NO$_2$ | H | CH$_3$ | CH$_3$ | H | H | H | H | 90 |
| 7 | —NO$_2$ | —Cl | H | CH$_3$ | CH$_3$ | H | H | H | H | 126 |
| 8 | —NO$_2$ | —Cl | H | H | H | CH$_3$ | CH$_3$ | H | H | 119 |
| 9 | —H | —H | 3-CF$_3$O | H | H | CH$_3$ | CH$_3$ | H | H | oil |
| 10 | —Cl | —F | H | H | H | CH$_3$ | CH$_3$ | H | H | oil |
| 11 | —Cl | —SO$_2$CH$_3$ | H | H | i-C$_3$H$_7$ | H | H | H | H | oil |
| 12 | —NO$_2$ | —H | H | CH$_3$ | CH$_3$ | H | H | H | H | oil |
| 13 | —NO$_2$ | —H | H | H | CH$_3$ | H | H | CH$_3$ | CH$_3$ | oil |
| 14 | —NO$_2$ | —Cl | H | CH$_3$ | H | H | H | CH$_3$ | CH$_3$ | oil |
| 15 | —Cl | —NO$_2$ | H | CH$_3$ | CH$_3$ | H | H | CH$_3$ | H | oil |
| 16 | —Cl | —Cl | H | i-C$_3$H$_7$ | H | H | H | H | H | oil |
| 17 | —Cl | —SO$_2$CH$_3$ | H | CH$_3$ | CH$_3$ | H | H | H | H | oil |
| 18 | —Cl | —SO$_2$CH$_3$ | H | CH$_3$ | CH$_3$ | H | H | H | CH$_3$ | oil |
| 19 | —NO$_2$ | —H | H | CH$_3$ | CH$_3$ | CH$_3$ | H | H | H | oil |
| 20 | —NO$_2$ | —Cl | H | H | H | H | CH$_3$ | CH$_3$ | CH$_3$ | oil |
| 21 | —Cl | —NO$_2$ | H | CH$_3$ | CH$_3$ | CH$_3$ | H | H | H | oil |
| 22 | —Cl | —SO$_2$CH$_3$ | H | CH$_3$ | CH$_3$ | CH$_3$ | H | H | H | oil |
| 23 | —NO$_2$ | —H | H | H | H | H | H | H | H | 142 |
| 24 | —H | —H | 3-NO$_2$ | H | H | H | H | H | H | 87 |
| 25 | —H | —H | 3-NO$_2$ | H | H | CH$_3$ | CH$_3$ | H | H | 82 |
| 26 | —F | —H | 6-F | H | H | H | H | H | H | 86 |
| 27 | —F | —H | 6-F | CH$_3$ | CH$_3$ | H | H | H | H | 95 |
| 28 | —F | —H | 6-F | H | H | CH$_3$ | CH$_3$ | H | H | oil |
| 29 | —OCH$_2$ | —H | 6-OCH$_3$ | H | H | CH$_3$ | CH$_3$ | H | H | 153 |
| 30 | —NO$_2$ | —H | 5-Cl | H | H | H | H | H | H | 165 |
| 31 | —NO$_2$ | —H | 5-Cl | H | H | H | H | CH$_3$ | CH$_3$ | 122 |
| 32 | —NO$_2$ | —H | 5-Cl | H | H | CH$_3$ | CH$_3$ | H | H | 132 |
| 33 | —NO$_2$ | —H | 5-Cl | H | CH$_3$ | H | H | CH$_3$ | CH$_3$ | 119 |
| 34 | —Cl | —SO$_2$CH$_3$ | H | H | H | CH$_3$ | CH$_3$ | H | H | 138–139 |
| 35 | —NO$_2$ | —H | H | H | H | CH$_3$ | CH$_3$ | H | H | 132–134 |
| 36 | —Cl | —Cl | H | H | H | H | H | H | H | 102–104 |
| 37 | —Cl | —F | H | H | H | H | H | H | i-C$_3$H$_7$ | oil |
| 38 | —NO$_2$ | —Cl | H | H | H | H | H | i-C$_3$H$_7$ | H | 108 |
| 39 | —NO$_2$ | —H | H | i-C$_3$H$_7$ | H | H | H | H | H | 99 |
| 40 | —NO$_2$ | —H | 4-CH$_3$ | H | H | H | H | H | H | 96 |
| 41 | —NO$_2$ | —CF$_3$ | H | H | H | H | H | H | H | 112 |
| 42 | —H | —F | H | H | H | H | H | H | H | 192 |
| 43 | —F | —H | H | H | H | H | H | H | H | 215 |

C. Biological Examples

1. Pre-emergence effect on weeds

Seeds or rhizome pieces of monocotyledon and dicotyledon weed plants are placed in sandy loamsoil in plastic pots and covered with soil. Weeds which occur in rice growing are grown in waterlogged soil, for which purpose the pots are filled with such an amount of water that the water stands up to the soil surface, or a few millimeters above. The active substance combinations according to the invention which are formulated in the form of wettable powders or emulsion concentrates, and, in parallel trials, the correspondingly formulated individual active substances, are then applied to the surface of the soil cover in the form of aqueous suspensions or emulsions at an application rate of 600 to 800 l of water/ha (converted), in various dosages. When applied to rice crops, the active substance formulations are poured into the irrigation water.

After the treatment, the pots are placed in a greenhouse and kept under good growth conditions for the weeds. After the test plants had emerged, the damage to the plants or the negative effect on the emergence was scored visually after a test period of 3 to 4 weeks by comparison with untreated controls. The herbicidal agents according to the invention have a good herbicidal pre-emergence action against a broad range of grass weeds and dicotyledon weeds.

In all cases there were differences between the calculated degree of effectiveness of the combinations and the found degree of effectiveness. The calculated degree of effectiveness of a combination which would have theoretically been expected is determined using S. R. Colby's formula: Calculation of synergistic and antagonistic responses of herbicide combinations, Weeds 15 (1967) 20–22.

In this formula $$E = X + Y - \frac{X \cdot Y}{100}$$

the abbreviations denote:

X = % damage by herbicide A at an application rate of x kg/ha;
Y = % damage by herbicide B at an application rate of y kg/ha;
E = damage to be expected by herbicides A+B at x+y kg/ha.

If the actual damage is greater than the damage to be expected by calculation, then the action of the combination is superadditive, i.e. there is a synergistic effect of action.

The active substance combinations according to the invention have a herbicidal action which is greater than would have been expected, using Colby's formula, on the basis of the actions observed when the individual components were applied alone. The active substance combinations are therefore synergistic (cf. test results in Table 3).

The active substance combinations according to the invention which are formulated as wettable powders or emulsion concentrates and, in parallel tests, the correspondingly formulated individual active substances, are sprayed in various dosages on the green parts of the plants at an application rate of 300 to 600 1 of water/ha (converted) and, after the test plants have remained in the greenhouse for about 3 to 4 weeks under ideal growth conditions, the effect of the preparations is scored visually by comparison with untreated controls. In the case of weeds which occur in rice growing, the active substances are also added directly to the irrigation water (application analogously to the so-called granule treatment) or sprayed onto plants and into the irrigation water. The agents according to the invention also have a good herbicidal post-emergence effectiveness against a broad range of economically important

TABLE 3

Herbicidal action, pre-emergence treatment

| Herbicide | Dose of a.i./ha | % action in Rice (transplanted) | Rice (sown) | ECCG | CYMO |
|---|---|---|---|---|---|
| Ia | 20 | 5 | 20 | 75 | 99 |
|  | 5 | 0 | 0 | 0 | 97 |
|  | 1,25 | 0 | 0 | 0 | 0 |
| IV | 250 | 0 | 35 | 99 | 70 |
|  | 60 | 0 | 10 | 90 | 0 |
|  | 15 | 0 | 0 | 25 | 0 |
| Ia + IV | 20 + 60 | 0 | 5 | 99 (98) | 99 (99) |
|  | 5 + 60 | 0 | 5 | 97 (90) | 99 (97) |
|  | 5 + 15 | 0 | 0 | 80 (25) | 99 (97) |
|  | 1 + 15 | 0 | 0 | 45 925) | 80 (0) |
| VIII | 100 | 0 | 30 | 92 | 35 |
|  | 25 | 0 | 15 | 30 | 0 |
|  | 6,25 | 0 | 15 | 0 | 0 |
| Ia + VIII | 20 + 25 | 0 | 15 | 95 (83) | 99 (99) |
|  | 5 + 25 | 0 | 0 | 90 (30) | 98 (97) |
|  | 5 + 6,25 | 0 | 5 | 60 (0) | 97 (97) |
| VII | 400 | 5 | 30 | 99 | 50 |
|  | 100 | 0 | 10 | 88 | 50 |
|  | 25 | 0 | 10 | 20 | 0 |
| Ia + VII | 5 + 100 | 0 | 10 | 100 (88) | 100 (99) |
|  | 5 + 25 | 0 | 5 | 70 (20) | 99 (97) |
|  | 1 + 25 | 0 | 0 | 55 (20) | 80 (0) |

Abbreviations:
ECCG = Echinochloa crus galli;
CYMO = Cyperus monti = C. serotinus
( ) = values calculated using Colby's formula
Ia = 2-(2-chloro-4-methylsulfonylbenzoyl)-1,3-cyclo-hexanedione
IV = quinchlorac
VII = butachlor
VIII = pretilachlor Abbreviations:

ECCG = Echinochloa crus galli;
CYMO = Cyperus monti—C. serotinus
( ) = values calculated using Colby's formula
Ia = 2-(2-chloro-4-methylsulfonylbenzoyl)-1,3-cyclohexanedione
IV = quinchlorac
VII = butachlor
VIII = pretilachlor 2. Post-emergence effect on weeds Seeds or rhizome pieces of monocotyledon and dicotyledon weeds are placed in sandy loam soil in plastic pots, covered with soil and grown in a greenhouse under good growth conditions. Weeds which occur in rice growing are grown in pots in which water covers the soil surface by up to 2 cm, and grown during the test phase. The test plants are treated in the three-leaf stage three weeks after sowing.

grass weeds and dicotyledon weeds. According to Colby's analysis (cf. Biological Example 1.), the actions of the agents according to the invention are synergistic (see Table 4).

TABLE 4

| Herbicide | Dose of a.i.g/ha | Herbicidal action (%), post-emergence treatment Rice (transplanted) | Rice (sown) | ECCG | CYMO |
|---|---|---|---|---|---|
| Ia | 20 | 0 | 0 | 0 | 97 |
|  | 5 | 0 | 0 | 0 | 93 |
|  | 1,25 | 0 | 0 | 0 | 0 |
| III | 120 | 0 | 0 | 100 | 10 |
|  | 30 | 0 | 0 | 100 | 0 |
|  | 8 | 0 | 0 | 0 | 0 |
| Ia + III | 20 + 30 | 0 | 0 | 100 (100) | 99 (97) |
|  | 5 + 30 | 0 | 0 | 100 (100) | 97 (93) |
|  | 1,25 + 8 | 0 | 0 | 60 (0) | 45 (0) |
| V | 1000 | 0 | 0 | 90 | 75 |
|  | 250 | 0 | 0 | 78 | 75 |
|  | 60 | 0 | 0 | 0 | 10 |

TABLE 4-continued

| Herbicide | Dose of a.i.g/ha | Rice (trans-planted) | Rice (sown) | ECCG | CYMO |
|---|---|---|---|---|---|
| Ia + V | 20 + 250 | 0 | 0 | 95 (90) | 99 (99) |
|  | 5 + 250 | 0 | 0 | 85 (78) | 98 (98) |
|  | 5 + 60 | 0 | 0 | 65 (0) | 96 (94) |
| VI | 250 | 0 | 0 | 83 | 0 |
|  | 60 | 0 | 0 | 0 | 0 |
|  | 15 | 0 | 0 | 0 | 0 |
| Ia + VI | 20 + 60 | 0 | 0 | 85 (0) | 99 (97) |
|  | 5 + 60 | 0 | 0 | 50 (0) | 95 (93) |
|  | 5 + 15 | 0 | 0 | 25 (0)) | 95 (93) |

Abbreviations:
see Table 2 and
III = fenoxaprop-ethyl
V = molinate
VI = thiobencarb Abbreviations:
see Table 2 and
III=fenoxaprop-ethyl
V=molinate
VI=thiobencarb 3. Tolerance by crop plants In further greenhouse experiments, seeds of a substantial number of crop plants and weeds are placed in sandy loam soil and covered with soil. Rice is reared and grown in waterlogged soil as paddy rice.

Some of the pots are treated immediately as described under 1., and the remaining pots are placed in the greenhouse until the plants have developed two to three true leaves, and then sprayed with various dosages of the active substance combinations according to the invention and, for comparison reasons, with only one intermediate active substance, as described under 2. In the case of paddy rice, the application was also carried out by pouring the active substances, or their formulation, into the irrigation water.

Visual scoring four to five weeks after the application and after the plants had been in the greenhouse revealed that the active substance combinations according to the invention did not inflict any damage to various cultures when used as a pre- or post-emergence treatment even when high dosage rates of active substances were used. They left Gramineae crops such as, for example, barley, wheat, rye, sorghum species and, in particular, maize and rice, unharmed. The active substance combinations according to the invention therefore have a high selectivity when used for controlling undesired plant growth in agricultural crops.

Compared with the application of the individual active substances alone, it emerges, in particular also at high dosage rates, that the selectivity of the active substance combinations compared with the individual active substances is better than the most effective of each of the herbicides, when applied at the same dosage rate. The active substance combinations are therefore suitable for effectively reducing herbicide damage to crop plants, in particular in rice.

We claim:

1. A herbicidal agent which comprises a synergistically effective amount of one or more compounds of the general formula (I) or of salts

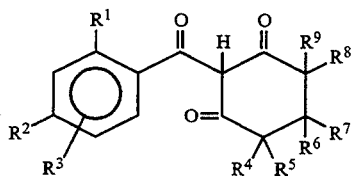

where
R$^1$ is halogen, (C$_1$-C$_4$)alkoxy, (C$_1$-C$_4$)haloalkyl, —NO$_2$, —CN or S(O)$_n$R$^{10}$;
R$^2$ and R$^3$ independently of one another are hydrogen, halogen, (C$_1$-C$_4$)alkyl, C$_1$-C$_4$)alkoxy, (C$_1$-C$_4$)haloalkoxy, (C$_1$-C$_4$) haloalkyl, —CN, —NO$_2$, —S(O)$_n$—R$^{11}$, —NR$^{12}$R$^{13}$, —NR$^{14}$—CO—R$^{15}$ or —CO—R$^{16}$;
R$^4$, R$^6$, R$^7$, R$^8$ and R$^9$ independently of one another are hydrogen or (C$_1$-C$_4$)alkyl;
R$^5$ is hydrogen, (C$_1$-C$_4$)alkyl or —CO—O—(C$_1$-C$_4$)alkyl;
R$^{10}$ is (C$_1$-C$_4$)alkyl, (C$_1$-C$_4$)haloalkyl or (C$_1$-C$_4$)alkoxy;
R$^{11}$ is (C$_1$-C$_4$)alkyl, (C$_1$-C$_4$)haloalkyl, phenyl, benzyl or —NR$^{17}$R$^{18}$;
R$^{12}$ and R$^{13}$ independently of one another are hydrogen or (C$_1$-C$_4$)alkyl;
R$^{14}$ is hydrogen or (C$_1$-C$_4$)alkyl;
R$^{15}$ is (C$_1$-C$_4$)alkyl;
R$^{16}$ is hydrogen, (C$_1$-C$_4$)alkyl, (C$_1$-C$_4$)haloalkyl or (C$_1$-C$_4$)-alkoxy;
R$^{17}$ and R$^{18}$ independently of one another are hydrogen or (C$_1$-C$_4$-alkyl and
n and m independently of one another are 0, 1 or 2, in a synergistically effective combination with one or more of the following compounds II–III (type B compounds), the type A and type B compounds being present in a ratio by weight of from about 1:0.5 to 1:200:

Ethyl C-2-[4-(6-chlorobenzoxazol-2-yloxy)phenoxy]-propionate (II),

Ethyl D,L-2-[4-(6-chlorobenzoxazol-2-yloxy)-phenoxy]-propionate (III),

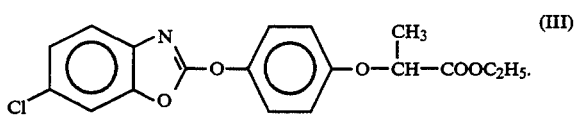

2. The agent as claimed in-claim 1, which comprises compounds of the formula (I) or salts thereof, where
R$^1$ is fluorine, chlorine, bromine, iodine, methoxy, nitro, cyano or —S(O)$_n$R$^{10}$,
R$^2$ and R$^3$ independently of one another are hydrogen, fluorine, chlorine, bromine, iodine, methyl, methoxy, trifluoromethoxy, cyano, nitro, trifluoromethyl, —SO$_2$R$^{11}$, —NR$^{12}$R$^{13}$, —N(CH$_3$)—CO—R$^{14}$ or —CO—O—(C$_1$-C$_4$)alkyl and
R$^4$, R$^5$, R$^6$, R$^7$, R$^8$ and R$^9$ independently of one another are hydrogen or methyl and
R$^{10}$, R$^{11}$, R$^{12}$, R$^{13}$, R$^{14}$ and n are as defined above.

3. The agent as claimed in claim 1 or 2, which comprises one or more compounds of the formula (I) or salts thereof, where
R$^2$ and R$^3$ independently of one another are hydrogen, fluorine, chlorine, bromine, —N(CH$_3$)$_2$, methoxy, nitro, —SO$_2$CH$_3$, —SO$_2$CH$_2$Cl, —SO$_2$N(CH$_3$)$_2$ or trifluoromethyl and n is 2, and R$^1$, R$^4$, R$^5$, R$^6$, R$^7$, R$^8$ and R$^9$ are as defined above.

4. The agent as claimed in claim 1 which comprises, besides customary formulation auxiliaries, 0.1 to 99% by weight of the active substances of types A and B.

5. A process for the preparation of an agent as claimed in claim 1, which comprises formulating one or more compounds A with one or more compounds B in analogy to a customary formulation, of plant protection agents, selected from the group consisting of wettable powders, water-soluble powders, emulsifiable concentrates, aqueous solutions or concentrates, emulsions, sprayable solutions (tank mix), capsule suspensions, dispersions on an oil or water base, suspoemulsions, suspension concentrates, dusting powders, solutions which can be mixed with oils, seed-dressing agents, micro-granules, spray granules, coated granules, adsorption granules, granules for soil application and for broadcasting, water-dispersible granules, ULV formulations, microcapsules or waxes.

6. A method for controlling weeds, which comprises applying an effective amount of an agent as claimed in claim 1 to these weeds or the areas under cultivation on which they grow.

7. The method as claimed in claim 6, wherein weeds are selectively controlled in crops.

8. The method as claimed in claim 7, wherein the crop is selected from the group consisting of wheat, barley, rye, rice and maize.

9. The agent as claimed in claim 1, wherein the type A compound is 2-(2-chloro-4-methylsulfonylbenzoyl)-1,3-cyclohexanedione, and the type B compound is ethyl D-2-[4-(6-chlorobenzoxazol-2-yloxy)phenoxy]-propionate.

10. The agent as claimed in claim 1, wherein the type A compound is 2-(2-chloro-4-methylsulfonylbenzoyl)-1,3-cyclohexanedione, and the type B compound is ethyl D,L-2-[4-(6-chlorobenzoxazol-2-yloxy)phenoxy]-propionate.

11. A process for the preparation of an agent as claimed in claim 1, which comprises formulating one or more compounds A with one or more compounds B in analogy to a customary formulation of plant protection agents, selected from the group consisting of dusting agents, wettable powders, dispersion concentrates, emulsifiable concentrates, and water dispersable granules.

12. A method for controlling weeds, which comprises the post-emergent application of an effective amount of the agent as claimed in claim 1 to these weeds.

13. The method as claimed in claim 6, wherein weeds are selectively controlled in rice crops.

* * * * *

UNITED STATES PATENT AND TRADEMARK OFFICE
CERTIFICATE OF CORRECTION

PATENT NO. : 5,447,903
DATED : September 5, 1995
INVENTOR(S) : Ort et al.

It is certified that error appears in the above-indentified patent and that said Letters Patent is hereby corrected as shown below:

IN THE CLAIMS:

In Claim 1, column 18, line 41, instead of "Ethyl C-2" please insert --Ethyl D-2--.

Signed and Sealed this

Fourteenth Day of May, 1996

Attest:

BRUCE LEHMAN

Attesting Officer　　　Commissioner of Patents and Trademarks